United States Patent
Laufer et al.

(10) Patent No.: US 10,065,925 B2
(45) Date of Patent: Sep. 4, 2018

(54) CARBODIIMIDES, METHOD FOR THE PRODUCTION AND USE THEREOF

(71) Applicant: LANXESS Deutschland GmbH, Cologne (DE)

(72) Inventors: Wilhelm Laufer, Ellerstadt (DE); Volker Wenzel, Heddesheim (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 15/524,118

(22) PCT Filed: Nov. 3, 2015

(86) PCT No.: PCT/EP2015/075612
§ 371 (c)(1),
(2) Date: May 3, 2017

(87) PCT Pub. No.: WO2016/071347
PCT Pub. Date: May 12, 2016

(65) Prior Publication Data
US 2017/0334839 A1   Nov. 23, 2017

(30) Foreign Application Priority Data
Nov. 4, 2014 (EP) ..................................... 14191710

(51) Int. Cl.
*C08K 5/29* (2006.01)
*C07C 275/40* (2006.01)
*C07C 267/00* (2006.01)
*C07C 263/06* (2006.01)

(52) U.S. Cl.
CPC .......... *C07C 275/40* (2013.01); *C07C 263/06* (2013.01); *C07C 267/00* (2013.01); *C08K 5/29* (2013.01)

(58) Field of Classification Search
CPC ... C07C 275/40; C07C 263/06; C07C 267/00; C08K 5/29
USPC .......................................................... 524/195
See application file for complete search history.

(56) References Cited

U.S. PATENT DOCUMENTS

| | | | |
|---|---|---|---|
| 3,502,722 A | 3/1970 | Neumann | |
| 4,076,945 A | 2/1978 | Elmer | |
| 5,210,170 A * | 5/1993 | Quiring | ................. C08G 18/10 252/182.2 |
| 5,498,747 A | 3/1996 | Pohl et al. | |
| 5,597,942 A | 1/1997 | Pohl et al. | |
| 6,498,225 B2 | 12/2002 | Tebbe et al. | |
| 2012/0123062 A1 | 5/2012 | Laufer et al. | |
| 2013/0190443 A1 | 7/2013 | Margraf et al. | |

FOREIGN PATENT DOCUMENTS

| | | |
|---|---|---|
| DE | 1130594 B | 5/1962 |
| EP | 2262000 B1 | 3/2016 |

OTHER PUBLICATIONS

European Search Report from European Patent Application No. 14191710, dated Apr. 14, 2015, two pages.

* cited by examiner

*Primary Examiner* — Hui H Chin

(57) ABSTRACT

The invention relates to novel carbodiimides having terminal urea and/or urethane groups, to processes for the production thereof and to the use thereof as a stabilizer in ester-based polymers especially in films for protection from hydrolytic degradation.

20 Claims, No Drawings

CARBODIIMIDES, METHOD FOR THE PRODUCTION AND USE THEREOF

The invention relates to novel carbodiimides having terminal urea and/or urethane groups, to processes for the production thereof and to the use thereof as a stabilizer in ester-based polymers especially in films for protection from hydrolytic degradation.

BACKGROUND INFORMATION

Carbodiimides have proven useful in many applications, for example as hydrolysis inhibitors for ester-based thermoplastics, polyols, polyurethanes, etc.

It is preferable to use sterically hindered aromatic monocarbonyl diamides therefor. Especially 2,6-diisopropylphenylcarbodiimide is well known in this connection. However, these carbodiimides have the disadvantage of being volatile even at low temperatures. They are thermally unstable and can eliminate volatile substances (offgassing). Other carbodiimides, as described in EP 0 628 541 A1, are based on special raw materials which are costly to obtain. They also have high viscosities at room temperature which impedes handling of these carbodiimides. Furthermore, in certain PU, PET, PLA or lubricant applications, their reactivity and/or their stabilizing effect is insufficient at the concentrations used as standard. Polymeric carbodiimides based on inexpensive raw materials, such as those described in DP-2248751 and U.S. Pat. No. 2,941,983, are not sufficiently sterically hindered and do not show a good hydrolysis-inhibiting effect.

SUMMARY

The present invention therefore has for its object the provision of novel, sterically hindered, easily producible and easily processable carbodiimides which show high thermal stability and very low offgassing and may be employed especially in film applications.

It was found that, surprisingly, this object was achieved by employing certain aromatic carbodiimides.

DETAILED DESCRIPTION OF THE EMBODIMENTS

The present invention accordingly provides carbodiimides having terminal urea and/or urethane groups of formula (I)

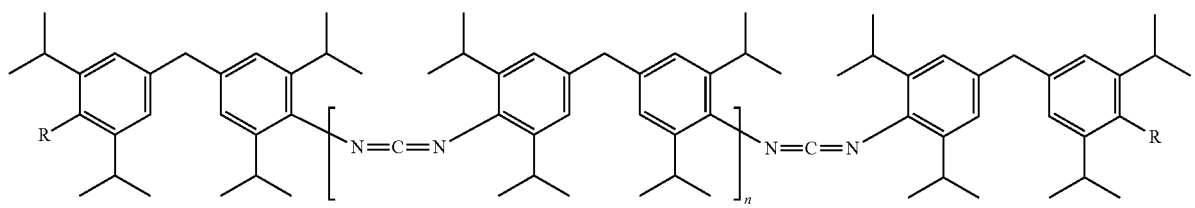

where
R may be identical or different and is selected from the group of —NHCONHR$^I$, —NHCONR$^I$R$^{II}$ and —NHCOOR$^{III}$ radicals, wherein R$^I$ and R$^{II}$ are identical or different and represent a $C_1$-$C_{22}$-alkyl, $C_6$-$C_2$-cycloalkyl, $C_6$-$C_{18}$-aryl or $C_7$-$C_{18}$-aralkyl radical and R$^{III}$ represents a $C_1$-$C_{22}$ alkyl, preferably $C_1$-$C_6$-alkyl, particularly preferably methyl, ethyl, or i-propyl, $C_6$-$C_{12}$-cycloalkyl, preferably $C_6$-cycloalkyl, $C_6$-$C_{18}$-aryl or $C_7$-$C_{18}$-aralkyl radical, and an unsaturated alkyl radical (for example an oleyl radical) having 2-22, preferably 12-20, particularly preferably 16-18, carbon atoms, or an alkoxypolyoxyalkylene radical, and n=0 to 20, preferably n=1 to 15.

The carbodiimide content (NCN content, measured by titration with oxalic acid) of the b carbodiimides according to the invention is preferably 2-10 wt %.

The term $C_7$-$C_{18}$-aralkyl radical is to be understood as meaning that the aryl radical is bonded via an alkyl functionality to the nitrogen in the end group R in the case of R$^I$ and R$^{II}$ and to the oxygen in the end group R in the case of R$^{III}$.

Preferred alkoxypolyoxyalkylene radicals are polyethylene glycol monomethyl ethers having molar masses of 200-600 g/mol, particularly preferably of 350-550 g/mol.

Preference is given to carbodiimides of formula (I) where R=—NHCOOR$^{III}$ radical where R$^{III}$ is alkoxypolyoxyalkylene or an unsaturated alkyl radical having 18 carbon atoms and n=0 to 20, preferably n=1 to 10, particularly preferably n=2 to 5, very particularly preferably n=3 to 6.

The carbodiimide content of these preferred carbodiimides is preferably 2-8 wt %, particularly preferably 3-6 wt %, very particularly preferably 4-5 wt %.

Likewise preferred are carbodiimides of formula (I) where R=—NHCOOR$^{III}$, wherein R$^{III}$ is $C_1$-$C_{22}$-alkyl, preferably $C_1$-$C_6$-alkyl, particularly preferably methyl, ethyl or i-propyl, $C_6$-$C_{12}$-cycloalkyl, preferably $C_6$-cycloalkyl, and n=0 to 15, preferably n=1 to 15, particularly preferably n=2 to 10, very particularly preferably n=3 to 8.

The carbodiimide content of these preferred carbodiimides is preferably 2-10 wt %, particularly preferably 3-10 wt %, very particularly preferably 4-8 wt %.

Furthermore, the carbodiimides according to the invention preferably have average molar masses (Mw) of 1000-10 000 g/mol, preferably 2000-8000 g/mol, particularly preferably 3000-6000 g/mol.

Preference is further given to carbodiimides having a polydispersity D=Mw/Mn of 1.2-2.5, particularly preferably of 1.4-1.8.

The purview of the invention encompasses all the hereinabove and hereinbelow recited general or preferred definitions of radicals, indices, parameters and elucidations among themselves, i.e. including between the respective ranges and preferences in any desired combination.

The present invention further provides for the production of the carbodiimides according to the invention by carbodiimidization of aromatic diisocyanates of formula (II)

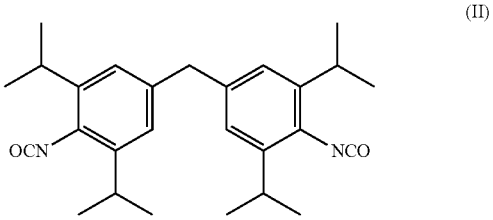

(II)

to eliminate carbon dioxide at temperatures of 80° C. to 200° C. in the presence of catalyst and optionally solvent and subsequent end-functionalization of the free NCO groups with primary or secondary amines and/or alcohols and/or alkoxypolyoxyalkylene alcohols.

The aromatic diamines required for the production of the diisocyanates may—as is known to one skilled in the art—be produced by a Friedel-Crafts alkylation of the corresponding 4,4'-diaminodiphenylmethane with propene. The aromatic diamines are commodity compounds, available for example from Lonza AG under the trade name Lonzacure® M-DIPA.

These diamines are subsequently reacted with phosgene to afford the corresponding diisocyanate of formula (II), M-DIPI.

To produce the carbodiimides according to the invention the diisocyanates of formula (II), M-DIPI, may advantageously be subjected to a condensation reaction at elevated temperatures, preferably temperatures of 80-200° C., particularly preferably of 100° C. to 180° C., very particularly preferably of 140-160° C., in the presence of catalysts to eliminate carbon dioxide. Processes suitable therefor are described for example in DE-A 1130594 and DE-A 11564021.

In one embodiment of the invention phosphorus compounds are preferred as catalysts for the production of the compounds of formula (I). Phosphorus compounds used are preferably phospholene oxides, phospholidenes or phospholine oxides and the corresponding phospholene sulfides. Also usable as catalysts are tertiary amines, basic metal compounds, alkali metal and alkaline earth metal oxides or hydroxides, alkoxides or phenoxides, metal carboxylate salts and non-basic organometallic compounds.

The carbodiimidization may be performed either in the absence or in the presence of a solvent. Preferably employed solvents are alkylbenzenes, paraffin oils, polyethylene glycol dimethyl ethers, ketones or lactones.

When the reaction mixture has the desired content of NCO groups, corresponding to an average degree of condensation of n=0 to 20, preferably n=1 to 10, the polycarbodiimidization is typically terminated.

The free terminal isocyanate groups of the carbodiimides are then reacted with primary or secondary aliphatic and/or aromatic amines, alcohols and/or alkoxypolyoxyalkylene alcohols, preferably in a slight excess of —NH, —NH$_2$ and/or —OH groups, optionally in the presence of a PU catalyst known to one person skilled in the art, preferably tert, amines or organotin compounds, particularly preferably DBTL (dibutyltin dilaurate) or DOTL (dioctyltin dilaurate). The amount of substance ratio of amines, alcohols and/or alkoxypolyoxyalkylene alcohols to carbodiimides is preferably 1.005-1.05:1, particularly preferably 1.01-1.03:1, based on the N=C=O groups present.

Preferred alcohols are ethanol and cyclohexanol.

In a further embodiment of the present invention to interrupt the carbodiimidization the temperature of the reaction mixture is reduced to 50-120° C., preferably 60-100° C., particularly preferably to 80-90° C. and optionally after addition of a solvent preferably selected from the group of alkylbenzenes, particularly preferably toluene, the free terminal isocyanate groups of the carbodiimides are reacted with aliphatic and/or aromatic amines, alcohols and/or alkoxypolyoxalkylene alcohols preferably in a slight excess of —NH, —NH$_2$ and/or —OH groups optionally in the presence of a PU catalyst known to one skilled the art, preferably tert. amines or organotin compounds, particularly preferably DBTL (dibutyltin dilaurate) or DOTL (dioctyltin dilaurate). The amount of substance ratio of amines, alcohols and/or alkoxypolyoxyalkylene alcohols to carbodiimides is preferably 1.005-1.05:1, particularly preferably 1.01-1.03:1, based on the N=C=O groups present.

After complete reaction the catalyst, and optionally the solvent, is preferably distilled off at temperatures of 80-200° C. under reduced pressure.

Preferred alcohols are ethanol and cyclohexanol.

The present invention additionally provides a further process for producing the carbodiimides according to the invention by a partial, preferably <50%, end-functionalization of the free NCO groups with primary or secondary amines or alcohols and/or alkoxypolyoxyalkylene alcohols in the aromatic diisocyanates of formula (II)

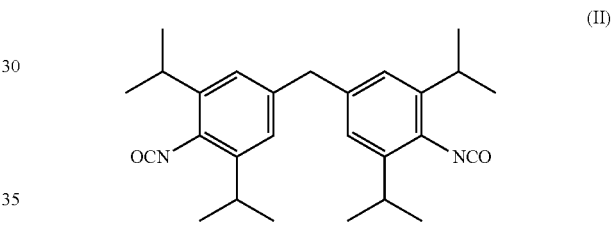

(II)

and subsequent carbodiimidization to eliminate carbon dioxide at temperatures of 80° C. to 200° C. in the presence of catalysts and optionally solvent.

The carbodiimides according to the invention are preferably purified after preparation thereof. Purification of the crude products may be effected by distillation and/or by extraction with solvents and/or by recrystallization in solvents. Suitable solvents for purification which may be employed with preference are polyethylene glycol dimethyl ethers, akylbenzenes, paraffin oils, alcohols, ketones or esters. These are commodity solvents.

The present invention further provides a preferred process for producing the inventive carbodiimide of formula (I) where R=—NHCOOR$^{III}$, wherein R$^{III}$ is C$_1$-C$_{22}$-alkyl, preferably C$_1$-C$_6$ alkyl, particularly preferably methyl, ethyl or i-propyl, C$_6$-C$_{12}$-cycloalkyl, particularly preferably C$_6$-cycloalkyl, and n=0 to 20, preferably n=1 to 15, particularly preferably n=2-10, very particularly preferably n=3 to 8, where after carbodiimidization and optionally purification the melt is preferably pelletized on pelletizing belts. Both customary pelletizing systems and customary granulating systems may be employed. These are obtainable for example from Sandvik Holding GmbH or GMF Gouda.

The inventive carbodiimides of formula (I) where R=—NHCOOR$^{III}$, wherein R$^{III}$ is cyclohexyl, are very particularly suitable.

The present invention further provides a composition comprising
 at least one ester-based polymer, and
 at least one inventive carbodiimide of formula (I).

The ester-based polymers are preferably polyester polyols, ester-based thermoplastic polyurethanes, ester-based polyurethane elastomers or foams, polyethylene terephthalate (PET), polybutylene terephthalate (PST), polytrimethylene terephthalate (PIT), copolyesters, such as preferably modified polyesters made of cyclohexanediol and terephthalic acid (PCTA), thermoplastic polyester elastomers (TPE E), ethylene vinyl acetate (EVA), polylactic acid (PLA) and/or PLA derivatives, polyhydroxyalkanoates (PHA), polybutylene adipate terephthalate (PBAT), polybutylene succinate (PBS), in polyimide (PA) such as polyamide 6, 6.6, 6.10, 6.12, 10, 11, 12 for example or in blends, such as preferably PA/PET or PHA/PLA blends. These are commercially available polymers.

The concentration of the inventive carbodiimides of formula (I) in the composition according to the invention is preferably 0.1-10 wt %, preferably 1-5 wt %, particularly preferably 1-3 wt %.

The present invention additionally provides a process for producing the composition according to the invention, where the inventive carbodiimides of formula (I) where R=—NHCOOR$^{III}$, where R$^{III}$ is $C_1$-$C_{22}$-alkyl, preferably $C_1$-$C_6$-alkyl, particularly preferably methyl, ethyl or i-propyl, $C_6$-$C_{12}$-cycloalkyl, preferably $C_6$-cycloalkyl, and n=0 to 20, preferably n=1 to 15, particularly preferably n=2 to 10, very particularly preferably n=3 to 8, are added by means of solids metering units to the ester-based polymers selected from the group comprising polyethylene terephthalate (PET), polybutylene terephthalate (PBT), polytrimethylene terephthalate (PTT), thermoplastic polyurethanes (TPU), copolyesters, such as the modified polyester made of cyclohexanediol and terephthalic acid (PCTA), thermoplastic polyester elastomers (TPE E), ethylene vinyl acetate (EVA), polybutylene adipate terephthalate (PBAT), polybutylene succinate (PBS), polylactic add (PLA) and/or PLA derivatives, polyhydroxyalkanoates (PHA), in polyamide (PA) such as polyamide 6, 6.6, 6.10, 6.12, 10, 11, 12 for example or in blends, for example PA/PET or PHA/PLA blends.

Solids metering units in the context of the invention are preferably: single-, twin- and multi-screw extruders, continuous co-kneaders (Buss-type) and discontinuous kneaders, e.g. Banbury-type and other units customary in the polymer industry.

The polyester polyol ester-based polymers are preferably long-chain compounds preferably having a molecular weight (in g/mol) of up to 2000, preferably between 500-2000 and particularly preferably between 500-1000.

The term "polyester polyol" in the context of the invention encompasses both long-chain diols and triols, and also compounds having more than three hydroxyl groups per molecule.

It is advantageous when the polyester polyol has an OH number of up to 200, preferably between 20 and 150 and particularly preferably between 50 and 115. Especially suitable are polyester polyols being reaction products of various polyols with aromatic or aliphatic dicarboxylic acids and/or polymers of lactones.

The polyester polyols employed in the context of the inventions are commodity compounds obtainable from Bayer MaterialScience AG under the trade names Baycoll® and Desmophen®.

The present invention additionally provides for the use of the carbodiimides according to the invention in ester-based polyols, polyethylene terephthalate (PET), polybutylene terephthalate (PBT), polytrimethylene terephthalate (PTT), copolyesters, such as the modified polyester made of cyclohexanediol and terephthalic acid (PCTA), thermoplastic polyester elastomers (TPE E), ethylene vinyl acetate (EVA), polylactic acid (PLA) and/or PLA derivatives, polyhydroxyalkanoates (PHA), polybutylene adipate terephthalate (PBAT), polybutylene succinate (PBS), in polyamid (PA) such as polyamide 6, 6.6, 6.10, 6.12, 10, 11, 12 for example or in blends, for example PA/PET- or PHA/PLA-Blends, in thermoplastic polyurethanes (TPU), in polyurethane elastomers, in PU adhesives, in PU casting resins, in PU foams or in PU coatings for wood, leather, synthetic leather and textiles as protection from hydrolytic degradation.

The present invention additionally provides films comprising at least one polyester selected from the group polyethylene terephthalate (PET), ethylene vinyl acetate (EVA), polyethylene naphthalate (PEN), polybutylene terephthalate (PBT), polytrimethylene terephthalate (PTT) and/or polycyclohexanedimethanol terephthalate (PCT) and 1.0 3.0 wt % of at least one inventive carbodiimide based on the polyester.

Production of the film is preferably effected by mixing of the inventive carbodiimide or optionally of a carbodiimide masterbatch with the polyester in the melt and subsequent melt extrusion, see also EP-A 2262000.

The following apparatuses may be employed for melt extrusion: single-screw, twin-screw or multi-screw extruders, planetary extruders, cascade extruders, continuous co-kneaders (Buss-type) and discontinuous kneaders, e.g. Banbury-type and other units customary in the polymer industry.

The films may be produced in any desired thickness. However, film thicknesses between 25 and 300 micrometers are preferred.

The present invention additionally provides for the use of the film according to the invention in solar cells, where it is preferably used for sealing and thus for protecting from environmental influences, for example moisture and ingress of foreign objects.

The invention further also provides molding materials made of polyamide (PA) comprising 1.0-3.0 wt % of the inventive carbodiimide based on the polyamide and optionally further additives and fillers and/or reinforcers, preferably glass fibers.

Polyamides preferred in accordance with the invention are semicrystalline or amorphous polyamides producible from diamines and dicarboxylic acids and/or lactams having at least 5 ring atoms or corresponding amino acids. Contemplated reactants are preferably aliphatic and/or aromatic dicarboxylic acids, particularly preferably adipic acid, 2,2,4-trimethyladipic acid, 2,4,4-trimethyladipic acid, azelaic acid, sebacic acid, isophthalic acid, terephthalic acid, aliphatic and/or aromatic diamines, particularly preferably tetramethylenediamine, pentamethylenediamine, hexamethylenediamine, 1,9-nonanediamine, 2,2,4- and 2,4,4-trimethylhexamethylenediamine, the isomeric diaminodicyclohexylmethanes, diaminodicyclohexylpropanes, bisaminomethylcyclohexane, phenylenediamine, xylylenediamine, amino carboxylic acids, in particular aminocaproic acid, or the corresponding lecterns. Copolyamides of a plurality of the monomers mentioned are included.

Particular preference is given to polyamide 6 or polyamide 6.6, polyamide 6.6 being employed with very particular preference.

Proportions of recycled polyamide molding materials and/or fiber recyclates may also be present.

The polyamides preferably have a relative viscosity of 22 to 4.0, particularly preferably of 2.7 to 3.5, wherein the relative viscosity may be determined/measured on a 1 wt % solution in m-cresol at 25° C.

Additives in the context of the present invention are stabilizers, antistats, flow assistants, demolding agents, flame retardant additives, emulsifiers, nucleating agents, plasticizers, glidants, dyes, pigments, branching agents, chain extenders or additives for increasing electrical conductivities. The additives may be used alone or in admixture/ in the form of masterbatches.

Fillers or reinforcers may be employed individually or else as mixtures of two or more different fillers and/or reinforcers. Preference is given to using fillers and/or reinforcers selected from talc, mica, silicate, quartz, titanium dioxide, wollastonite, kaolin, amorphous silicas, magnesium carbonate, chalk, feldspar, barium sulfate, glass beads and/or fibrous fillers and/or reinforcers based on carbon fibers and/or glass fibers. Particular preference is given to using mineral particulate fillers based on talc, mica, silicate, quartz, titanium dioxide, wollastonite, kaolin, amorphous silicas, magnesium carbonate, chalk, feldspar, barium sulphate and/or glass fibers.

Very particular preference is given to using mineral particulate fillers based on talc, wollastonite, kaolin and/or glass fibers.

Especial preference is further also given to using acicular mineral fillers. In accordance with the invention the term acicular mineral fillers is to be understood as meaning a mineral filler having a highly pronounced acicular character. Examples include acicular wollastonites. This mineral preferably has a length diameter ratio of 2:1 to 35:1, particularly preferably of 3:1 to 19:1, especially preferably of 4:1 to 12:1. The average particle size of the acicular minerals according to the invention is preferably less than 20 µm, particularly preferably less than 15 µm, especially preferably less than 10 µm, determined with a CILAS GRANULOMETER.

The employed filler and/or reinforcer may also be surface-modified as described in EP-A 2562219.

The glass fibers employable with especial preference according to the invention may either have a circular cross section and a filament diameter of 6 to 18 µm, preferably between 9 and 15 µm, or a flat shape and noncircular cross section whose principal cross sectional axis has a width in the range of 6-40 µm and whose secondary cross sectional axis has a width in the range of 3-20 µm. The glass fiber is preferably selected from the group of E-glass fibers, A-glass fibers, C-glass fibers, D-glass fibers, S-glass fibers and/or R-glass fibers.

The glass fibers may be added as endless fibers or as chopped or ground glass fibers. The fibers may be finished with a suitable size system, preferably comprising inter alia adhesion promoters based on silane in particular, as described for example in EP-A 2562219.

To finish the fillers it is preferable to employ silane compounds generally in amounts of 0.05 to 2 wt %, preferably 0.25 to 1.5 wt % and especially 0.5 to 1% wt %, based on the mineral filler for surface coating.

As a result of processing to afford the molding composition/the molded article, the particulate fillers in the molding composition/the molded article may have a smaller $d_{97}$ value/$d_{50}$ value than the originally employed fillers. As a result of processing to afford the molding material/molded article the glass fibers may have shorter length distributions in the molding material/molded article than originally used.

The examples which follow serve to elucidate the invention without providing a limiting effect.

Exemplary Embodiments

Tests were carried out on:
1) CDI (A): a carbodiimide according to formula (I) where R=NCO and n>20, having an NCN content of about 11 wt % and having an NCO content of <1 wt %, comparative.
2) CDI (B): a carbodiimide of formula (I) where R=—NHCOOR$^{III}$ and R$^{III}$=cyclohexyl, having and NCN content of about 6 wt % and n=about 3, inventive.

Production of Carbodiimide CDI (A), Comparative

A baked-out and nitrogen-filled 250 ml four-necked flask was initially charged under a nitrogen stream with 92 g of the diisocyanate of formula (II), M-DIPI. 50 mg of 1-methylphospholene oxide were added and the mixture heated to 160° C. Carbodiimidization was then performed at 160° C. with elimination of carbon dioxide until an NCO content of about 1 wt % had been achieved. The products obtained was no longer stirrable at 160°. Viscosity at 140° C. was >1000 Pas and pelletization was therefore not possible.

Production of the Inventive Carbodiimide CD (B)

A baked-out and nitrogen-filled 250 ml four-necked flask was initially charged under a nitrogen stream with 92 g of the diisocyanate of formula (II), M-DIPI. 50 mg of 1-methylphospholene oxide were added and the mixture heated to 160° C. Carbodiimidization was then performed at 160° C. with elimination of carbon dioxide until an NCO content of about 6 wt % had been achieved. The reaction mixture was then cooled to about 90-100° C. and the terminal NCO groups were reacted with cyclohexanol in toluene as solvent (free NCO content <0.1%). Distiliative removal of the toluene afforded a product having an NCN content of about 6 wt %. Said product was still very readily stirrable at 160° and was pelletized without any issues. Viscosity at 140° C. was <10 Pas. The average molar mass was about 3000 g/mol.

The results show that compared to the prior art the inventive carbodiimides show handleable viscosities in the melt thus making large industrial scale production possible. Moreover, said carbodiimides have the advantage that they are based on less costly raw materials.

What is claimed is:

1. A carbodiimide of formula (I) having terminal urea and/or urethane groups

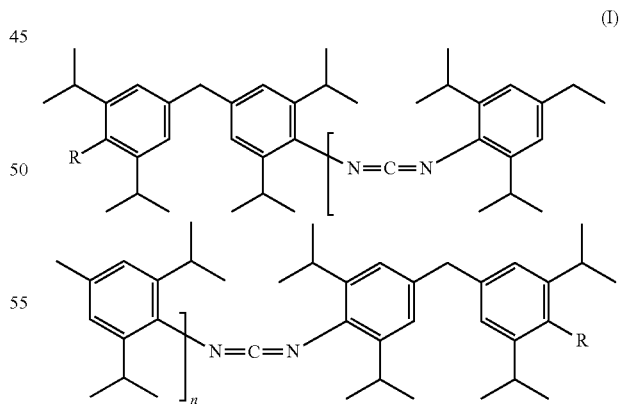

wherein:
each R may be Identical or different, and is selected from the group of —NHCONHR$^{I}$, —NHCONR$^{I}$R$^{II}$ and —NHCOOR$^{III}$ radicals, wherein
R$^{I}$ and R$^{II}$ are identical or different and represent a $C_1$-$C_{22}$-alkyl, $C_8$-$C_{12}$-cycloalkyl, $C_6$-$C_{18}$-aryl, or $C_7$-$C_{18}$-aralkyl radical, and $R^{III}$ represents a $C_1$-$C_{22}$-alkyl, $C_6$-$C_{12}$-cycloalkyl, $C_6$-$C_{16}$-aryl, $C_7$-$C_{18}$-aralkyl radical, an unsaturated alkyl radical having 2-22 carbon atoms, or an alkoxypolyoxyalkylene radical, and n=0 to 20.

2. The carbodiimide as claimed in claim 1, wherein:

R is an —NHCOOR$^{III}$ radical where R$^{III}$ is an alkoxypolyoxyalkylene or an unsaturated alkyl radical having 18 carbon atoms, and n=0 to 20.

3. The carbodiimide as claimed in claim 1, wherein:

R is an —NHCOOR$^{III}$ radical, wherein R$^{III}$ is $C_1$-$C_{22}$-alkyl, $C_6$-$C_{12}$-cycloalkyl, and n=0 to 15.

4. The carbodiimide as claimed in claim 2, wherein the NCN content in the carbodiimide is 2-8 wt %.

5. The carbodiimide as claimed in claim 3, wherein the NCN content in the carbodiimide is 2-10 wt %.

6. The carbodiimide as claimed in claim 1, wherein the carbodiimide has an average molar mass (Mw) of 1000-10,000 g/mol.

7. A process for producing the carbodiimides as claimed in claim 1, the process comprising:

carbodiimidizing diisocyanates of formula (II)

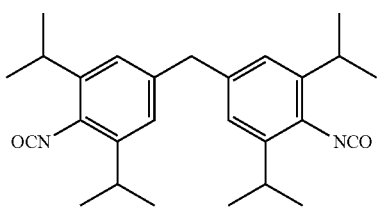

(II)

to eliminate carbon dioxide at temperatures of 80° C. to 200° C. in the presence of catalysts and optionally solvent, and subsequently, end-functionalizing free NCO functionalities with primary or secondary amines and/or alcohols.

8. A process for producing the carbodiimides as claimed in claim 1, the process comprising:

end-functionalizing a portion of free NCO groups of aromatic diisocyanates of formula (II)

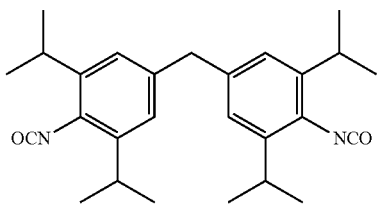

(II)

with primary or secondary amines and/or alcohols and/or alkoxypolyoxyalkylene alcohols, and subsequently, carbodiimidizing to eliminate carbon dioxide at temperatures of 80° C. to 200° C. in the presence of catalysts and optionally solvent.

9. A process for producing the carbodiimides as claimed in claim 3, the process comprising end-functionalizing and carbodiimidizing aromatic diisocyanates of formula (II)

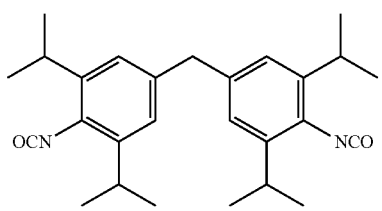

(II)

to produce a carbodiimide melt, and, after production of the melt, pelletizing the melt on pelletizing belts.

10. A composition comprising:

at least one carbodiimide as claimed in claim 1; and at least one ester-based polymer selected from the group of polyester polyols, ester-based thermoplastic polyurethanes, polyurethane elastomers, PU adhesives, PU casting resins, polyamides (PA), polyethylene terephthalates (PET), polybutylene terephthalates (PBT), polytrimethylene terephthalates (PTT), copolyesters, thermoplastic polyester elastomers (TPE E), ethylene vinyl acetates (EVA), polylactic acids (PLA), polybutylene adipate terephthalates (PBAT), polybutylene succinates (PBS), PLA derivatives, and/or polyhydroxyalkanoates (PHA).

11. The composition as claimed in claim 10, wherein the concentration of the carbodiimide is 0.1-10 wt %.

12. A process for producing the compositions as claimed in claim 10, the process comprising adding the carbodiimides by means of solids metering units to the ester-based polymers, wherein for the carbodiimides, R is an —NHCOOR$^{III}$ radical, wherein Rd is $C_1$-$C_{22}$-alkyl, or $C_6$-$C_{12}$-cycloalkyl, and n=0 to 15; and the ester-based polymer is selected from the group consisting of polyethylene terephthalate (PET), polybutylene terephthalate (PBT), polytrimethylene terephthalate (PTT), polyamides (PA), thermoplastic polyurethanes (TPU), copolyesters, modified polyester made of cyclohexanediol and terephthalic acid (PCTA), thermoplastic polyester elastomers (TPE E), ethylene vinyl acetate (EVA), polylactic acid (PLA), polybutylene adipate terephthalate (PBAT), polybutylene succinate (PBS), PLA derivatives and/or polyhydroxyalkanoates (PHA).

13. A method for protecting ester-based polymers from hydrolytic degradation, the method comprising adding the carbodiimides as claimed in claim 1 to ester-based polymers, wherein the ester-based Polymers are selected from the group consisting of polyols, polyamides (PA), polyethylene terephthalate (PET), polybutylene terephthalate (PBT), polytrimethylene terephthalate (PTT), copolyesters, thermoplastic polyester elastomers (TPE E), ethylene vinyl acetate (EVA), polylactic acid (PLA), PLA derivatives, polybutylene adipate terephthalates (PBAT), polybutylene succinates (PBS), polyhydroxyalkanoates (PHA), PA/PET or PHA/PLA blends, thermoplastic polyurethanes (TPU), polyurethane elastomers, PU adhesives, PU casting resins, PU foams, and PU coatings for wood, leather, synthetic leather and textiles.

14. A method for protecting polyester films, from hydrolytic degradation, the method comprising adding the carbodiimides as claimed in claim 1 to polyester, and extruding the polyester into films.

15. A film comprising at least one polyester selected from the group polyethylene terephthalate (PET), ethylene vinyl acetate (EVA), polyethylene naphthalate (PEN), polybutylene terephthalate (PBT), polytrimethylene terephthalate (PTT) and/or polycyclohexanedimethanol terephthalate (PCT) and 1.0-3.0 wt % of at least one carbodiimide as claimed in claim 1 based on the polyester.

16. A molding material made of polyamide (PA) and comprising:
- 1.0-3.0 wt % of the carbodiimide as claimed in claim 1 based on the polyamide, and optionally further additives, fillers and/or reinforcers.

17. The carbodiimide as claimed in claim 1, wherein:
R is an —NHCOOR$^{III}$ radical where R$^{III}$ is an alkoxy-polyoxyalkylene or an unsaturated alkyl radical having 18 carbon atoms, and
n=1 to 10;
the NCN content in the carbodiimide is 3-6 wt %; and
the carbodiimide has an average molar mass (Mw) of 2000-8000 g/mol.

18. The carbodiimide as claimed in claim 1, wherein:
R is an —NHCOOR$^{III}$ radical where R$^{III}$ is an alkoxy-polyoxyalkylene or an unsaturated alkyl radical having 18 carbon atoms;
n=3 to 6;
the NCN content in the carbodiimide is 4-5 wt %; and
the carbodiimide has an average molar mass (Mw) of 3000-6000 g/mol.

19. The carbodiimide as claimed in claim 1, wherein:
R is an —NHCOOR$^{III}$ radical, wherein R$^{III}$ is $C_1$-$C_6$-alkyl, or $C_6$-$C_{12}$-cycloalkyl;
n=1 to 15; and
the NCN content in the carbodiimide is 3-10 wt %; and
the carbodimide has an average molar mass (Mw) of 2000-8000 g/mol.

20. The carbodiimide as claimed in claim 1, wherein:
R is an —NHCOOR$^{III}$ radical, wherein R$^{III}$ is methyl, ethyl, 1-propyl, or $C_6$-cycloalkyl;
n=3 to 8; and
the NCN content in the carbodiimide is 4-5 wt %; and
the carbodiimide has an average molar mass (Mw) of 3000-6000 g/mol.

* * * * *